United States Patent
Menard

(10) Patent No.: US 6,231,554 B1
(45) Date of Patent: May 15, 2001

(54) ABSORBENT ARTICLE HAVING PRE-FORMED COMPLIANT GASKETS

(75) Inventor: Michael J. Menard, Doylestown, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 08/183,552

(22) Filed: Jan. 19, 1994

Related U.S. Application Data

(63) Continuation of application No. 07/766,699, filed on Sep. 27, 1991, now abandoned.

(51) Int. Cl.[7] .................................................. A61F 13/15
(52) U.S. Cl. .............................. 604/385.01; 604/385.23; 604/385.24; 604/385.28; 604/387
(58) Field of Search ............................... 604/385.2, 358, 604/378, 385.1, 386, 387, 389, 390, 385.23, 385.24, 385.28

(56) References Cited

U.S. PATENT DOCUMENTS

| | | | |
|---|---|---|---|
| 3,709,221 | * | 1/1973 | Riley . |
| 4,100,921 | * | 7/1978 | Schaar . |
| 4,576,600 | * | 3/1986 | Joa ........................................ 604/390 |
| 4,701,177 | * | 10/1987 | Ellis et al. ............................ 604/358 |
| 5,037,418 | * | 8/1991 | Kons et al. ........................... 604/387 |
| 5,064,421 | * | 11/1991 | Tracy ................................... 604/386 |
| 5,234,422 | * | 8/1993 | Sneller et al. ..................... 604/385.2 |

* cited by examiner

*Primary Examiner*—Dennis Ruhl
(74) *Attorney, Agent, or Firm*—James P. Barr

(57) ABSTRACT

An absorbent article is provided for use in the perineal area of the body. Compliant sealing gaskets are pre-formed to extend outward from the central portion of the article. The gaskets may be formed by looping a strip of material so as to form a compliant cuff which bears against the user's body in a comfortable manner. An elastic member placed in tension so as to impart an arcuate shape to the article may be placed inside a cavity formed by the cuff. The gaskets may be applied to an article having wings attached to the central portion so as to form pockets for retaining the elasticized portions of the panty crotch. The proximal ends of the gaskets are disposed outward of the pockets and the distance between the pockets is less than the width of the panty crotch so that the body facing said of the article is placed in tension.

4 Claims, 11 Drawing Sheets

ABSORBENT ARTICLE HAVING PRE-FORMED COMPLIANT GASKETS

This is a continuation of application Ser. No. 07/766,699, filed Sep. 27, 1991 now abandoned.

FIELD OF THE INVENTION

The current invention concerns an absorbent article for use in the perineal area of the body, such as sanitary napkins, incontinence pads, and the like. More specifically, the current invention concerns an absorbent article having preformed compliant sealing gaskets that serve to prevent leakage past the absorbent article and to improve the comfort and fit of the article.

BACKGROUND OF THE INVENTION

Traditionally, absorbent articles have included a central absorbent portion having a body facing side, a garment facing side, longitudinally extending sides and transverse ends. These articles generally include an absorbent core made of loosely associated hydrophilic materials, such as wood pulp, that is covered on the body facing side by a layer of body fluid pervious material and on the garment facing said by a layer of body fluid impervious material. These layers are sometimes sealed around the absorbent core by joining them together along the longitudinal sides of the article so as to form laterally extending flanges—see, for example U.S. Pat. No. 4,678,527 (Ulman). The layer forming the body facing side is sometimes formed from an apertured plastic film which gives the surface of the article a feeling of dryness against the skin.

Typically absorbent articles are held in place by pressure sensitive adhesive on the garment facing side which adheres to the inner crotch surface of the user's undergarment. The fit of such absorbent products may be improved by imparting an arcuate shape to the article in the longitudinal direction. This is typically accomplished by applying longitudinally extending elastic elements placed in tension to the article—see, for example U.S. Pat. No. 3,236,238 (Morse) and U.S. Pat. No. 4,432,823 (Moore).

One drawback of prior art absorbent articles in which the layers are joined by forming flanges, as previously discussed, is that although the flanges are flexible with respect to forces acting perpendicular to the plane of the flange, they are fairly rigid with respect to forces acting in-plane. Consequently, the flanges of such articles have a tendency to dig into the skin of the user, causing discomfort.

Another drawback arises if the aforementioned apertured plastic film is used. Typically, such film is used to cover the sides of the article which bear against the user's thighs, as well as the upward facing portion of the body facing surface that is subjected directly to the fluid flow. Experience has shown that although the apertured plastic film feels dry against the skin, when pressed against the user's thighs it produces the unpleasant hot and sticky feeling associated with plastics.

Typically, absorbent articles are subject to lateral leakage under certain circumstances—for example, if the article is locally not in contact with the perineum because of wrinkling or deformation of the article or if the flow exceeds the local absorbent capacity of the article. Such lateral leakage causes fluid to flow along the surface of the perineum to the user's legs resulting, at the least, in soiling of the undergarment. Accordingly, napkins having wings extending from the longitudinal sides have been developed to protect the undergarment crotch from soiling—for example, see U.S. Pat. No. 4,285,343 (McNair). Unfortunately, lateral leakage can result in flow down the user's legs that soils other articles of clothing not protected by the wings.

U.S. Pat. No. 4,589,876 (Van Tilburg) discloses a sanitary napkin having wings in which flexible axes are formed that allow the wings to be folded over the edges of the panty crotch. Each wing is joined to the central portion of the napkin along a preferential bending line. The width of the central portion is less than the span of the perineum so that the elastic in the panty crotch bends the wings upward around the preferential bending line. This bending action causes the wings to form walls that bear against the laterally outward surfaces of the perineum to produce a seal that is described as being gasket-like. Unfortunately, such articles suffer from several drawbacks.

First, since the article relies on the panty elastic to bend the wings upward around the laterally outward surfaces of the perineum at the preferential bending joints between the wings and the central portion, the maximum width of the central portion is limited to the width of the panty crotch. This limits the absorbent capacity of the napkin as well as its applicability to a large variety of user/panty sizes.

Second, since the wings are folded over the edges of the panty crotch, the seals formed thereby can extend beyond the edges of the crotch only by the thickness of the wings. As a result, optimal contact of the seal with the body will not be attained for all users since the seal does not extend a substantial distance beyond the edge of the crotch. Again, this limits the applicability of the napkin.

Third, although the preferential bending line and flexible axis give the wing flexibility in the direction normal to the plane of the wing, the wing is relatively stiff with respect to a compression force applied in the plane of the wing. Hence, the compliancy of the wings is low, resulting in discomfort due to the wings digging into the body.

Fourth, since the elastic portion of the crotch is disposed at the top of the wall formed by the wing, the force imposed by deformation of the elastic portion acts to press only the wing against the user's body. The elastic portion does not push the central portion of the article against the perineum so as to ensure proper contact.

U.S. Pat. No. 4,701,177 (Ellis et al.) discloses a napkin in which the absorbent core in the longitudinally middle portion of the napkin has a dog bone shape—that is, the thickness of the central portion is increased but its width is reduced—created by pinching in the sides of the absorbent core in the middle portion. The cover and barrier are joined along a joint line that follows the contour of the central absorbent. As a result, in the reduced width middle portion of the napkin, the portions of the cover and barrier outboard of the seal line form walls. Elastic members disposed within the walls cause them to extend upward above the body facing surface and into the crease at the sides of the pudendum so as to prevent leakage. However, this arrangement suffers from several drawbacks.

First, as a result of the placement of the joint lines at the top of the sides of the central portion, the walls have a tendency to fold inward about the joint lines in use so that they lay over the body facing surface, thereby reducing the effective area of the central absorbent portion. Second, creating the walls requires that the central portion be formed into a dog bone shape so that this sealing approach is not applicable to all types of napkins. Third, the materials that form the walls are limited to those suitable for napkin covers and barriers.

U.S. Pat. No. 4,695,278 (Lawson) discloses a diaper in which flaps are formed by extending the cover and barrier beyond the sides of the central portion and joining them together along longitudinally extending joint lines spaced transversely from the central portion sides. Elastic members are disposed within the flaps, forming members characterized as "gasketing cuffs." Members characterized as "barrier cuffs" are formed by attaching strips of material, folded over so as to form loops at their distal ends, to the flaps along the joint lines. Elastic members are disposed within the loops causing them to extend vertically upward above the body facing surface. Unfortunately, as a result of the length of the barrier cuffs and the spacing of the joint lines away from the sides of the central portion, in use the barrier cuffs, like the walls in the Ellis patent, have a tendency to fold inward about the joint lines so that they lay over the body facing surface, thereby reducing the effective area of the central absorbent portion.

Consequently, it would be desirable to provide an absorbent article that overcomes the aforementioned drawbacks associated with absorbent articles heretofore known in the art. Such an article should be capable of forming a gasket-like seal to prevent lateral leakage of fluid yet avoid reducing the effective area of the central absorbent and be adapted to fit properly regardless of the size of the user or the undergarment. In addition, although being adapted to press against the user's body, the gasket should have sufficient compliancy to provide a comfortable fit and the appropriate surface properties necessary to minimize the unpleasant sensation of such contact. It would also be desirable that such a gasket be advantageously adapted to winged articles so that the wings and the gaskets cooperated to ensure a good fit and proper contact of the gasket and the central portion with the body.

SUMMARY OF THE INVENTION

It is an object of the current invention to provide an absorbent article that prevents leakage of fluid past the article.

It is another object of the current invention that the article be suitable for use by users in a large range of sizes and with undergarments in a wide variety of sizes.

It is still another object that the article be formed into an arcuate shape.

It is yet another object that the article make good sealing contact with the user's body yet be comfortable.

These and other objects are accomplished in an absorbent article for use in the perineal area of the user's body to absorb fluid, having a longitudinally extending central portion and right and left hand approximately longitudinally extending gaskets for preventing lateral leakage of fluid. The central portion has (i) an absorbent core, (ii) a first layer covering at least a portion of the absorbent core and forming a body facing surface, the first layer having right and left approximately longitudinally extending edges, and (iii) a second layer covering at least a portion of the absorbent core and forming a second surface opposite the body facing surface, the second layer having right and left approximately longitudinally extending edges. Each of the gaskets comprises (i) a longitudinally extending portion of the first layer adjacent one of its the edges, (ii) a longitudinally extending portion of the second layer adjacent one of its the edges joined to the portion of the first layer so as to form a flange, and (iii) a strip of material enclosing at least a portion of the flange.

In one embodiment, the strips of material form cavities for imparting compliancy to the gaskets and for enclosing elastic elements that are placed in tension when applied to the article so as to impart an arcuate shape to the article.

In another embodiment, the gaskets are applied to a napkin having right and left hand wings, each having a base portion and a tip portion. The tip portions are adapted to fold over the crotch of the user's undergarment. The wings are attached at their respective bases to the gaskets, thereby forming right and left pockets for retaining the right and left elasticized portions, respectively, of the undergarment crotch. The proximal ends of the right and left hand gaskets are disposed outwardly from the right and left pockets, respectively, so that the gaskets extend beyond the pockets.

DESCRIPTION OF THE PREFERRED EMBODIMENT

Figure 1:
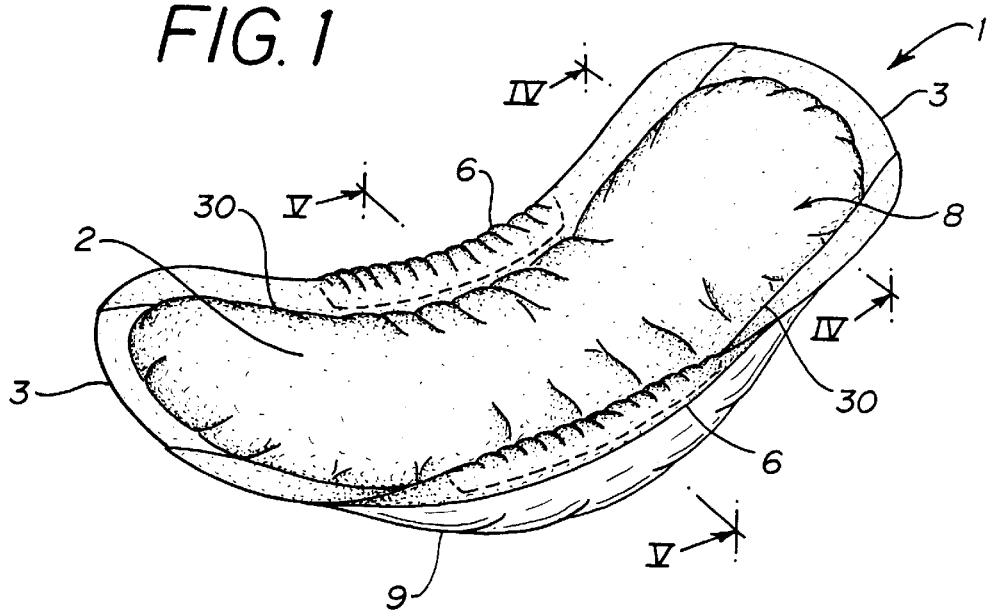
FIG. 1 is an isometric view of one embodiment of an absorbent article according to the current invention.
Figure 2:
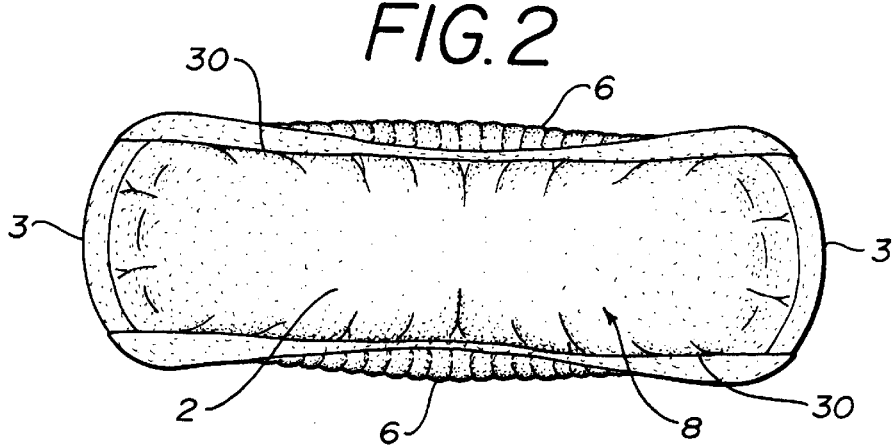
FIG. 2 is a plan view of the article shown in FIG. 1.
Figure 3:
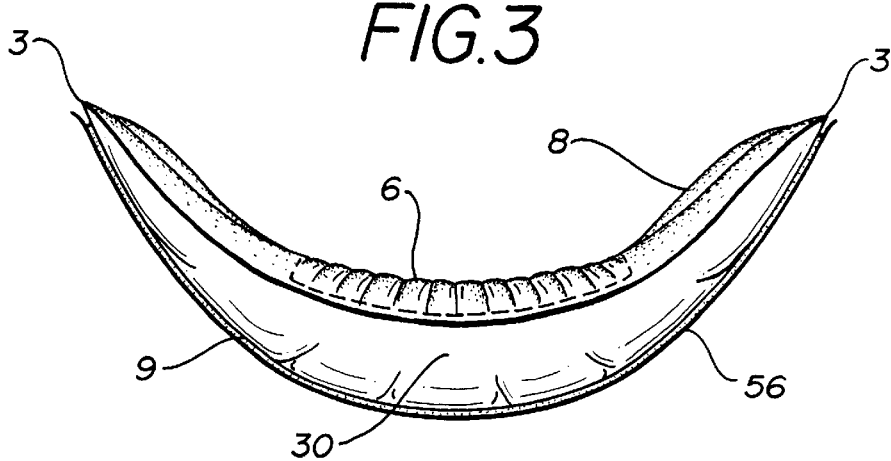
FIG. 3 is an elevation view of the article shown in FIG. 1.

There is shown in FIGS. 1–3 one embodiment of the current invention illustrated with respect to a sanitary napkin 1 according to the current invention. The napkin is comprised of a longitudinally extending central portion 2 having longitudinal sides 30 and transverse ends 3. The central portion may have an approximately rectangular shape, as shown, or an approximately oval shape. Alternatively, the sides 30 of the central portion 2 may be pinched-in somewhat to create an approximately dog bone shape.

Figure 4:
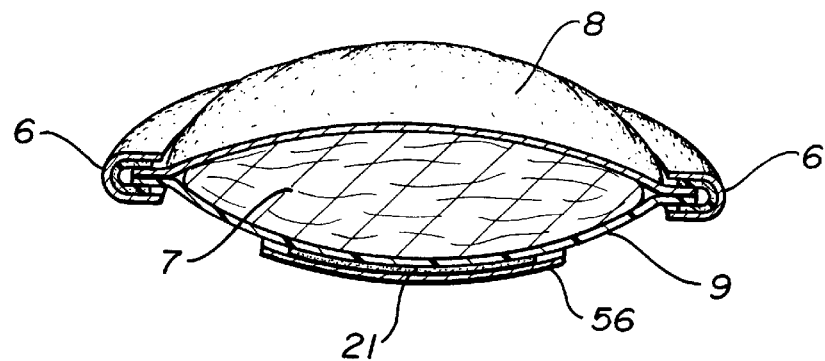
FIG. 4 is a transverse cross-section through the article shown in FIG. 1 taken through line IV—IV.
Figure 5:
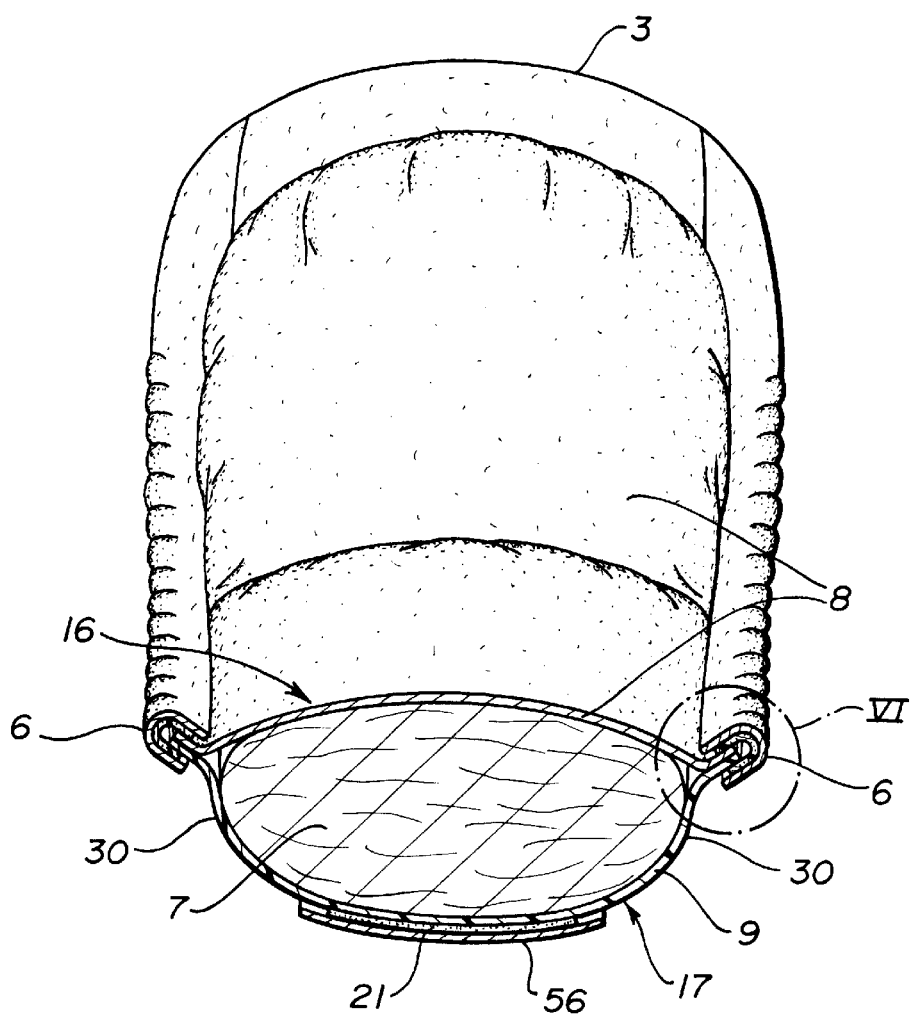
FIG. 5 is a transverse cross-section through the article shown in FIG. 1 taken through line V—V.

The construction the napkin 1 is shown in FIGS. 4 and 5. The central portion 2 of the napkin contains an absorbent core 7. As is known in the art, the absorbent core 7 may be comprised of a loosely associated absorbent hydrophilic material such as cellulose fibers, including wood pulp, regenerated cellulose fibers or cotton fibers, or other absorbent materials generally known in the art, including acrylic fibers, polyvinyl alcohol fibers, peat moss or super-absorbent materials.

The surface 16 of the napkin that is intended to be worn against the body of the user is covered by a layer 8 of a body-fluid pervious material, typically referred to as a "cover". The cover 8 may be formed from any fluid pervious material that is comfortable against the skin and that permits fluid to penetrate to the underlying core 7, which retains the fluid. The cover 8 should retain little or no fluid in its structure to provide a relatively dry surface next to the skin. The fluid pervious cover 8 may be a fibrous non-woven fabric made of fibers or filaments of polymers such as polyethylene, polypropylene, polyester or cellulose. Alternatively, the cover 8 may be formed from an apertured polymeric film. The thickness of the cover 8 will vary from approximately 0.001 to 0.062 inch, depending on the material chosen.

Generally, the fluid pervious cover 8 is a single, essentially rectangular sheet of material having a width sufficient to cover the body-facing surface 16 of the napkin. Preferably, the fluid pervious cover 8 is longer than the core 7 so as to form the transverse ends 3. The transverse ends 3 may be sealed with other pervious or non-pervious layers to fully enclose the core.

The napkin 1 further comprises a layer 9 of a body fluid impervious material, typically referred to as a "barrier", on its garment facing surface 17. The impervious barrier 9 may comprise any thin, flexible, body fluid impermeable material such as a polymeric film—for example, polyethylene, polypropylene, or cellophane or a normally fluid pervious material that has been treated to be impervious, such as impregnated fluid repellent paper or non-woven fabric material, or a flexible foam, such as polyurethane or cross-linked polyethylene. The thickness of the barrier when formed from a polymeric film typically is only 0.001 to 0.002 inch.

Generally, the barrier 9 is a single, essentially rectangular sheet of material having a width sufficient to cover the garment-facing surface 17 of the napkin. As shown in FIGS. 4–6, the fluid impervious barrier 9 may extend around the sides of the core 7 in a C-shaped configuration with the portions 10 of the barrier that are adjacent its longitudinal edges 32 extending upwardly from the garment facing surface 17 toward the body facing surface 16 so as to form a portion of the sides 30 of the central portion 2.

Figure 8:
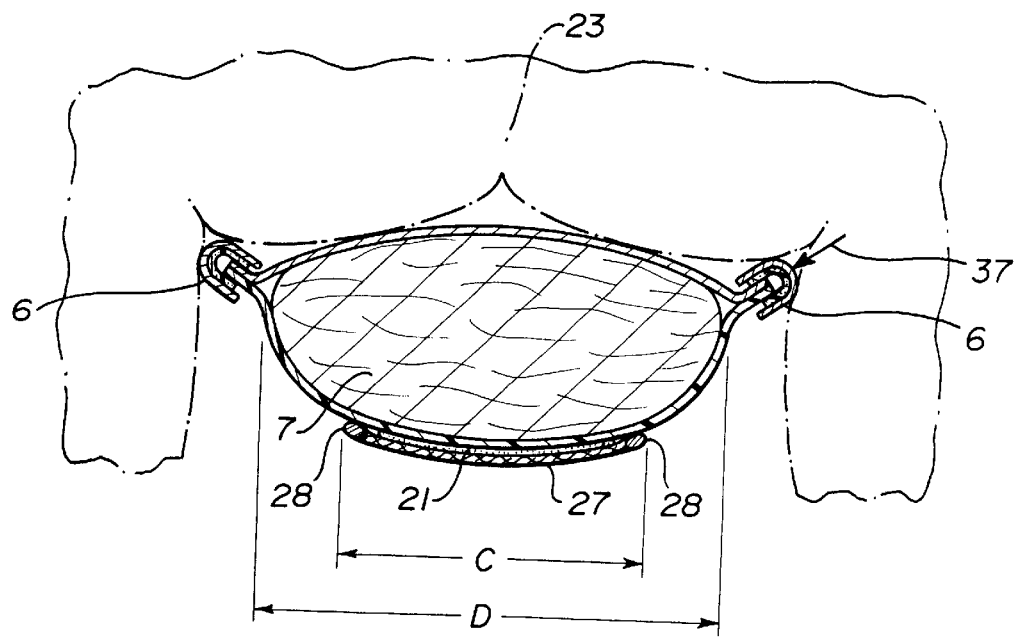
FIG. 8 is a transverse cross-section through the embodiment of the article shown in FIG. 1 in use.

The napkin 1 is applied to the crotch of a panty by placing the garment facing side of the napkin against the inside surface of the panty crotch 27, as shown in FIG. 8. Pressure sensitive adhesive strips 21 are applied to the garment facing side of the napkin to help maintain the napkin in place. As used herein, the term "pressure-sensitive adhesive" refers to any releasable adhesive or releasable tenacious means. Adhesive compositions suitable for sanitary napkins, include, for example, water-based pressure-sensitive adhesives such as acrylate adhesives. Alternatively, the adhesive may comprise rapid setting thermoplastic "hot melt", rubber adhesives or two-sided adhesive tape.

As is customary in the art, a paper release strip 56, which have been coated on one side, is applied to protect the adhesive strips 21 prior to use, as shown in FIGS. 4 and 5. The coating, which may be silicone, reduces the adherency to the adhesive of the coated side of the release strip. The release strip can be formed from any suitable sheet-like material which, when coated, adheres with sufficient tenacity to the adhesive to remain in place prior to use but which can be readily removed when the napkin is to be used.

As shown best in FIGS. 5 and 6, right and left hand longitudinally extending gaskets 6 are attached at their bases to the sides 30 of the central portion 2. According to the current invention, the distal ends 13 of the gaskets 6 may be contoured so as to conform to the user's body. Specifically, the width of the gaskets may vary so as to be greater in the center portion of the gasket's length than at it ends. Alternatively, the distal end 13 of the gasket 6 could be formed into a straight edge. As shown in FIGS. 1 and 2, the gaskets extend substantially the entire length of the napkin. However, it is preferred that the gaskets extend at least 50% of the napkin length.

Figure 6A:
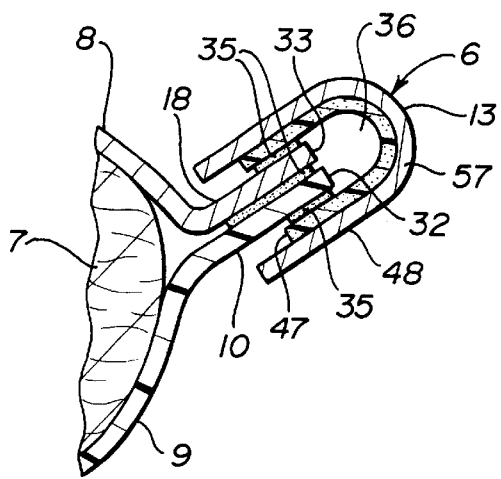
FIGS. 6a and 6b are detailed views of embodiments of the portion of the article shown in FIG. 5 enclosed by the circle VI.

As shown in FIGS. 5 and 6(a), each gasket 6 features a compliant cuff 48 formed by joining the portions 18 of the cover 8 adjacent its longitudinal edges 33 to the portions 10 of the barrier 9 adjacent its longitudinal edges 32 via an adhesive 35, thereby forming a flange, and enclosing the flange or joined portion in a strip of material 57 attached thereto via adhesive 35. The strip of material 48 may be formed from a fibrous non-woven flexible fabric that is soft and comfortable, such as silk, or that is cushiony, such as a high loft polyester. The strip of material 48 should also be non-wicking so as not to promote the flow of fluid beyond the gasket 6. Importantly, according to the current invention, the cuff material is not limited to that suitable for the cover, and may include laminates of pervious and impervious layers 38 and 39, respectively, as shown in FIG. 7(b). In addition to a comfortable "feel", the cuff 48 provides a smooth, curved, edgeless surface at the distal end 13 of the gasket 6 that serves as the contact surface for the gasket against the body, as shown in FIG. 8. Such contouring of the gasket contact surface minimizes any discomfort associated with contact under pressure.

Figure 6B:
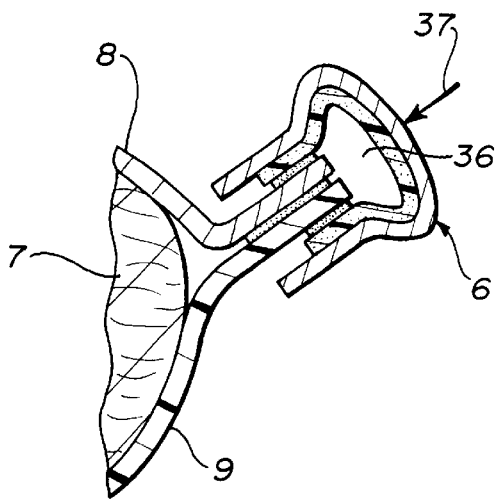

According to an important aspect of the current invention, the cuff 48 may be attached to the flange so as to form a loop which encloses a cavity 36, discussed further below. The gaskets 6 have several important advantages over prior art attempts to form sealing gaskets. The loop configuration of the cuff 48 gives the gasket 6 considerable compliancy. Thus, the rigidity and directional stability provided by the flanged portion of the gasket 6 is not obtained at the detriment of comfort. Specifically, the distal ends 13 of the gaskets are readily deformed by an inward force 37, imparted by the user's thighs, that acts in the plane of the gasket, as shown in FIG. 8. The force 37 is elastically absorbed by bending deformation of the loop so as to flatten the cavity 36, as shown in FIG. 6(b). It can be appreciated that although the gasket 6 remains in sealing contact with the body throughout a range of motion, the gasket imposes little noticeable resistance against the body until the cuff 48 has been completely flattened and the cavity 36 essentially eliminated. Moreover, those skilled in the art will appreciate that the compliancy of the gasket 6 can be varied by adjusting the size and shape of the cavity 36.

A further advantage of the flattening effect of the cuff 48 is that as the compression forces increase, the cuff geometry automatically adjusts itself so as to increase the area over which the contact force is distributed, thereby further minimizing the awareness of contact.

As shown in FIG. 5, in the longitudinally middle section of the napkin, the gaskets 6 are pre-formed to extend a distance above the body facing surface 16 of the central portion 2—specifically, above the portion of the body facing surface 16 that is adjacent the sides 30 of the central portion. According to the current invention, the distance by which the gaskets extend above the adjacent portion of the body facing surface 16 should be greater than zero to ensure that the gaskets 6 are placed into sealing contact with the user's body, as shown in FIG. 8. However, this distance must not be so great so that, notwithstanding the aforementioned directional stability, the gaskets 6 fold inwardly over the body facing surface 16 in use, thereby covering a substantial portion of the body facing surface and preventing it from passing fluid to the absorbent core 7.

As shown in FIG. 8, the elastic 28 in the panty crotch 27 need not press directly against the gaskets to extend them into sealing contact with the perineum. As a result, the width D of the central portion 2 can be greater than the width C of the panty crotch 27, as shown in FIG. 8, thereby permitting, if desired, the central portion to be sized to have maximum absorbency yet remain suitable for use with panties of any size.

In the preferred embodiment, the napkin 1 is curved in the longitudinal direction so that it has an arcuate shape, as shown in FIGS. 1 and 3, thereby better conforming the shape of the napkin to that of the body and improving the fit. Elastic members may be advantageously incorporated into the loop type gasket cuff 48 to create the arcuate shape. In the preferred embodiment, a layer of elastic polyurethane foam 47 is laminated to the interior surface of the cuff 48, as shown in FIG. 6(a).

In the preferred embodiment, the elastic foam 47 extends essentially the length of the gasket 6 and is attached to the gasket at its ends. However, in its undeformed state, the elastic member is shorter than the gasket 6 so that the elastic element is placed in tension by extending it at least 15% when it is attached to the ends of the gasket. When released, the elastic member returns to its approximate original length, thereby forcing the article into an arcuate shape. Alternatively, the length of the elastic member could span only a portion of the gasket length while still being placed in tension so as to impart an arcuate shape. In the preferred embodiment, the elastic member extends at least 30% of the length of the gasket.

Figure 7A:
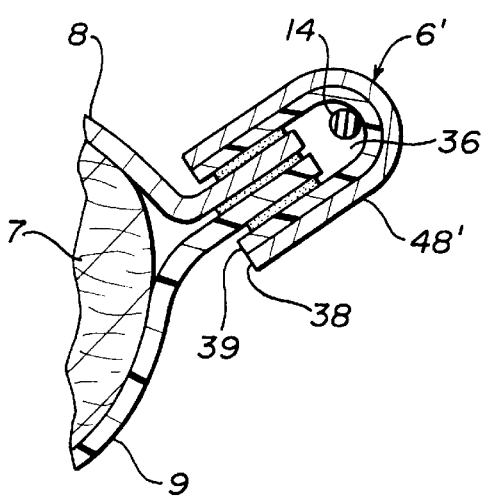
FIGS. 7a and 7b are detailed views of embodiments of the portion of the article shown in FIG. 5 enclosed by the circle VI.
Figure 7B:
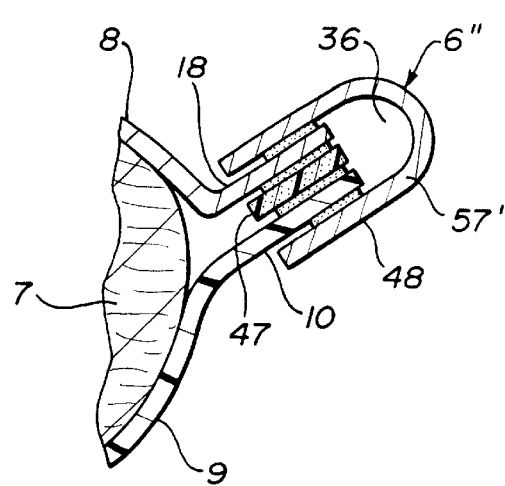

The elastic member may also be an elastic filament 14 disposed in the cavity 36 formed within the cuff 48 and attached thereto at its ends, as shown in FIG. 7(a) or the foam strip 47 may be disposed between the portions 18 and 10 of the cover and barrier that form the flange, as shown in FIG. 7(b). Alternatively, the strip of material 57' forming the cuff 48 could itself be an elastic foam applied to the napkin in tension, as shown in FIG. 7(b). In this case the stip of elastic foam 47 shown in FIG. 7(b) as being disposed within the flange could be eliminated.

The arcuate shape could also be imparted by applying to the gaskets heat shrinkable elements—such as filaments formed from vinylidene chloride copolymer microtape, as disclosed in U.S. Pat. No. 3,236,238 (Morse), hereby incorporated by reference in its entirety. Such filaments are heated after application to the gaskets, thereby causing them to shrink so as to impart an arcuate shape to the napkin.

Figure 22:
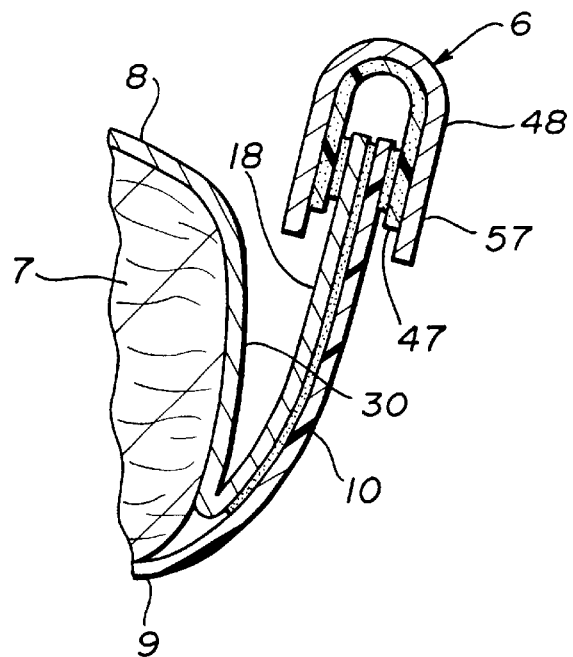
FIG. 22 shows an alternate embodiment of the gasket shown in FIG. 6.

In FIGS. 5 and 6, the flange portion is shown as beginning near the top of the side 30 of the central portion 2. However, as shown in FIG. 22, the flange could be formed by joining the portions 18 and 10 of the cover and base near the bottom of the side 30 and extending the flange upward therefrom to form the gasket.

Figure 9:
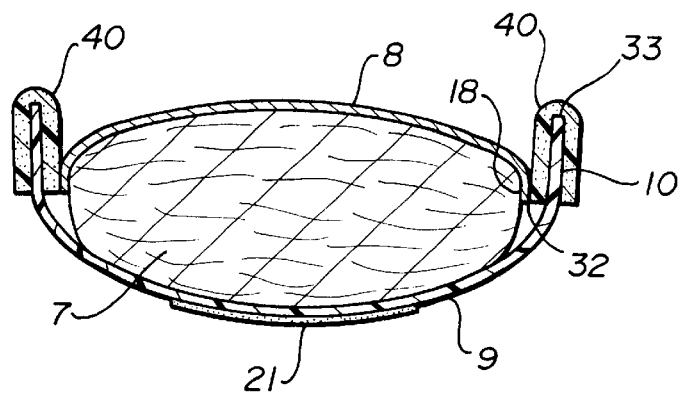
FIG. 9 is a transverse cross-section through a another embodiment of the article shown in FIG. 1.

An alternate embodiment of the napkin according to the current invention is shown in FIG. 9. According to this embodiment, the gasket is formed by a substantially flat strip 40 of a flexible resilient material attached at its proximal end to the central portion 2. The strip 40 may be formed from a cross-linked foam, such as VOLARA™, supplied by Voltek, a division of Sekisui America Corporation of Lawrence, Mass., having a thickness in the range of approximately 0.03 to 0.12 inch. The strip 40 is advantageously disposed between the portion 10 of the barrier 9 and the portion 18 of the cover 8 adjacent their longitudinal edges 32 and 33, respectively, and attached via adhesive to each. Moreover, as shown in FIG. 9, the barrier portion 10 may be extended so as to cover substantially all of the outward facing surface of the gasket, thereby further preventing leakage.

The central portion 2 of the napkin could be formed from an absorbent core having integral body facing and garment facing sides—that is, without separate layers of a body fluid pervious cover 8 and a body fluid impervious barrier 9. In this case, the gaskets would be formed by attaching the resilient flat strip 40 directly to the sides of the absorbent core.

Figure 10:
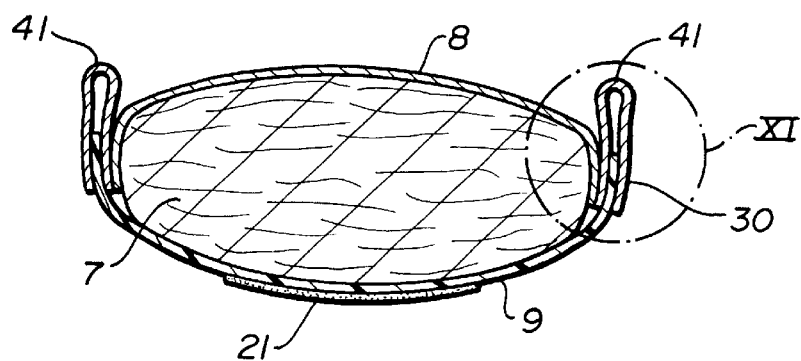
FIG. 10 is a transverse cross-section through a still another embodiment of the article shown in FIG. 1.

FIGS. 10 and 11 show another embodiment of the current invention. In this embodiment, the gasket 41 comprises a cuff 48 formed by bringing together the longitudinal edges of a strip of material 55 so as to form a loop. As shown in FIG. 11(a), the cuff 48 is attached to the sides 30 of the central portion 2 by joining, using adhesive 34, the interior surfaces of the strip 55 adjacent its longitudinal edges to the inward and outward facing surfaces of the portion 10 of the barrier 9 adjacent its longitudinal edge 32 so that the loop forms a cuff 48 that encloses the portion of the barrier adjacent its longitudinal edge. In addition, the outward facing surface of the portion 18 of the cover 8 that is adjacent its longitudinal edge 33 is joined to the inward facing surface of the cuff 48 by adhesive 34.

Figure 11A:
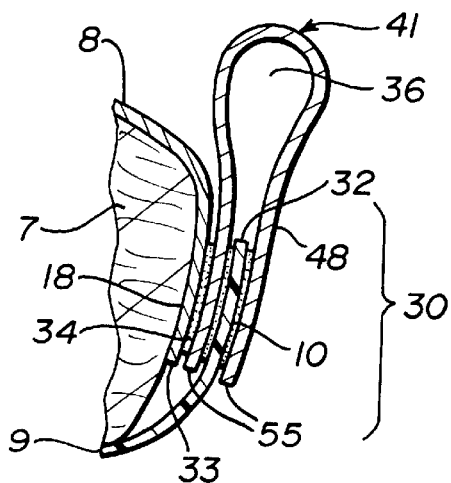
FIGS. 11 (a)–(d) are detailed views of embodiments of the portion of the article shown in FIG. 10 enclosed by the circle X.
Figure 11B:
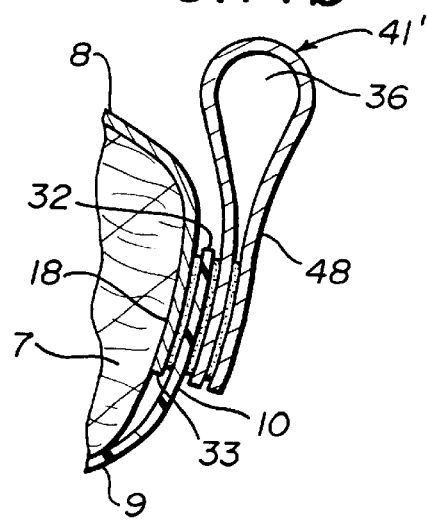
Figure 11C:
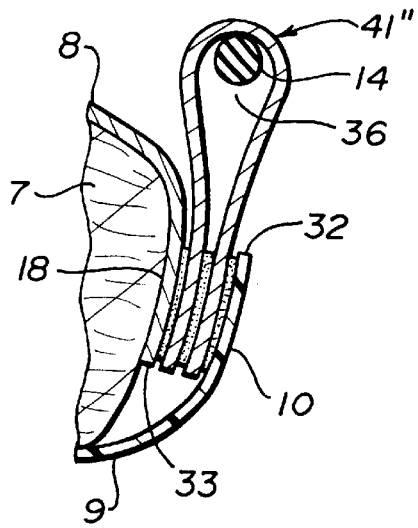

As shown in FIG. 11(b), the cuff 48 could be formed by joining the interior surfaces of the two portions of the strip of material 55 adjacent its longitudinal edges directly together, and then attaching the inward facing surface of cuff 48 to the outward facing surface of the portion 10 of the barrier 9 adjacent its longitudinal edge 32 and attaching the inward facing surface of the portion of the barrier adjacent its longitudinal edge to the outward facing surface of the portion 18 of the cover 8 adjacent its longitudinal edge 33 so that the portion 10 of the barrier 9 was disposed between the cuff and the portion 18 of the cover 8. Also, as shown in FIG. 11(c), the outward facing surface of the cuff 48 could be attached to the inward facing surface of the portion 10 of the barrier and the inward facing surface of the cuff attached to the outward facing surface of the portion 18 of the cover so that the cuff was disposed between the portions 10 and 18 of the barrier and cover, respectively.

Figure 11D:
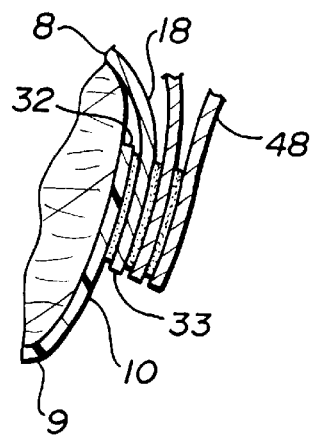

Alternatively, as shown in FIG. 11(d), the cuff 48 could be attached to the outward facing surface of the portion 18 of the cover 8 adjacent its longitudinal edge 33 and the inward facing surface of the portion of the cover adjacent its longitudinal edge attached to the outward facing surface of the portion 10 of the barrier 9 adjacent its longitudinal edge 32 so that the portion 18 of the cover 8 adjacent its longitudinal edge 33 is disposed between the cuff and the portion 10 of the barrier 9 adjacent its longitudinal edge 32.

Importantly, in each of the approaches to attaching the gaskets to the central portion 2 shown in FIGS. 10 and 11, the cuff 48 is attached to the napkin side 30 along a portion of the surfaces forming the sides of the cuff, rather than along its edges. Thus, at least a portion of each of the sides 30 of the central portion is formed from a laminate comprising layers of cuff, cover and barrier material. Unlike prior art attempts at forming gaskets, the cuffs are not attached along flexible joint lines adjacent the tops of the sides 30 of the central portion or transversely spaced apart from the sides 30, whcih would allow them to freely bend. Such prior art flexible joints have the undesirable characteristics of requiring the presence of elastic within the gaskets or contact between the elastic in the panty crotch and the gaskets in order to maintain them in the upright position. Such flexible joints also allow the gaskets to fold over the body facing surface 16 of the central portion, thereby reducing its effective area.

By contrast, the attachment method according to the embodiment of the current invention shown in FIGS. 10 and 11, gives adequate directional stability to the gaskets so that they will extend upward so as to make good sealing contact with the perineum without the incorporation of elastic members into the gaskets. Moreover, provided their length is not excessive, the directional stability of the attachment method according to the current invention will prevent the gaskets from folding over the body facing surface 16 in use.

As shown in FIG. 11, the loop type cuffs 48 form cavities that impart compliancy to the gasket 41, as previously discussed with respect to the embodiment shown in FIG. 6(a). Moreover, although, unlike some prior art gaskets, the gaskets according to the current invention do not require the presence of elastic members to cause them to extend upright, elastic members, such as those previously discussed with respect to the embodiment shown in FIGS. 6 and 7, may be advantageously incorporated into the loop type gasket cuff 48 to create the arcuate shape. FIG. 11(c) shows a gasket 41" in which an elastic filament 14 is disposed in the cavity 36.

Figure 12:
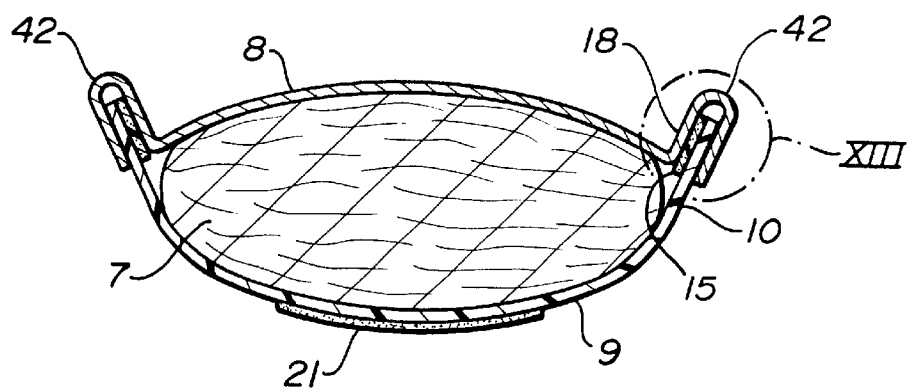
FIG. 12 is a transverse cross-section through a still another embodiment of the article shown in FIG. 1.

FIG. 12 shows still another embodiment of the current invention. In this embodiment, each gasket 42 is formed by extending the cover 8 so that the portion 18 adjacent its longitudinal edge 33 is wrapped around the portion 10 of the barrier adjacent its longitudinal edge 32, thereby forming a laminated cuff.

Figure 13A:
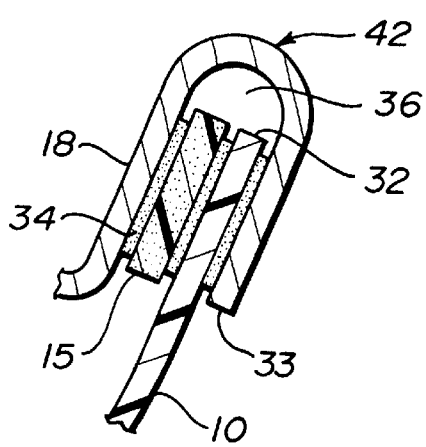
FIGS. 13 (a)–(c) are detailed views of embodiments of the portion of the article shown in FIG. 12 enclosed by the circle XIII.
Figure 13B:
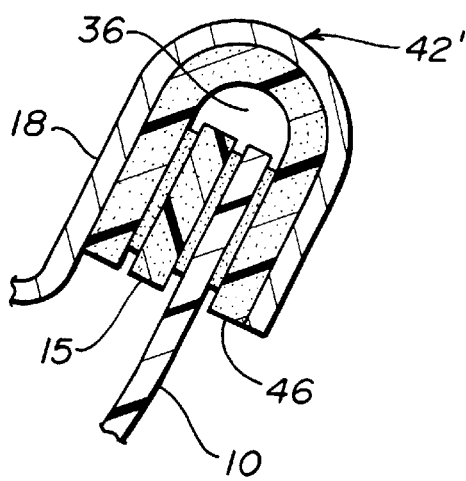
Figure 13C:
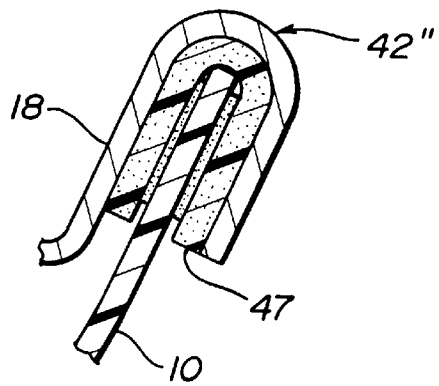

FIG. 13 shows three embodiments of the gaskets 42 shown in FIG. 12. As previously discussed, a cavity 36 can be formed inside the cuff so as to impart additional compliancy to the gasket 42. Moreover, a strip of elastic foam 15, placed in tension when applied to the napkin, can be disposed within the laminate to impart the aforementioned arcuate shape to the article. Additionally, a layer of foam 46 could be laminated to the inner surface of portion 18 of the cover 8 to further increase the compliancy of the gasket, as shown in the embodiment in FIG. 13(b). Alternatively, the foam 46 could be laminated to the outer surface of cover portion 18. As shown in FIG. 13(c), a strip of elastic foam 47 placed in tension can be wrapped around the barrier portion 10 to provide both compliancy and shaping. In the embodiment shown in FIG. 13(c), the cavity 36 has been eliminated, relying entirely on the foam strip 47 for compliancy.

Figure 23A:
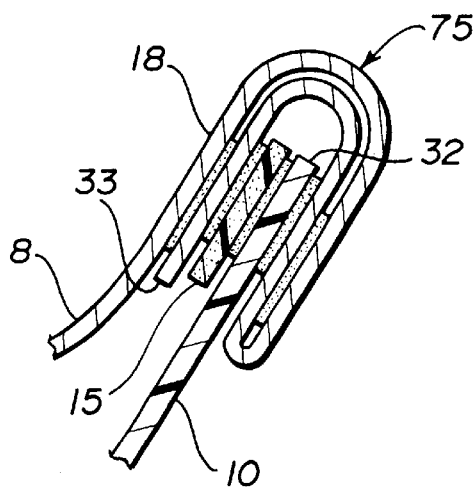
FIGS. 23a and 23b shows two alternative embodiments of the gasket shown in FIG. 13.

FIG. 23(a) shows another embodiment of the napkin shown in FIG. 12, in which the gasket 75 is formed by folding the portion 18 of teh cover over on itself before using it to enclose the portion 10 of the barrier, so that a double layer of the cover formed the gasket cuff.

Figure 23B:
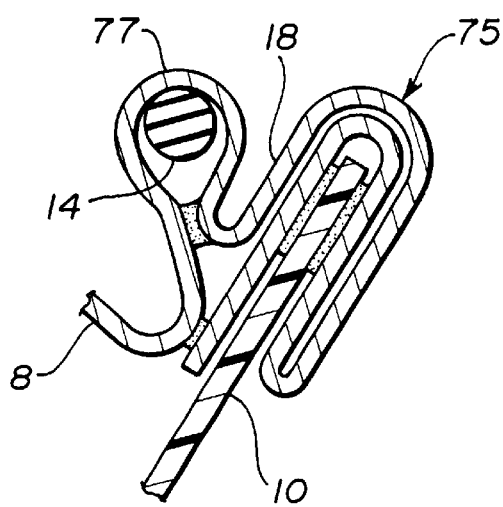

As shown in FIG. 23(b), an elastic element, attached to the napkin in tension, could be disposed within a secondary loop formed within the folded over portion of the cover portion 18 so as to form a secondary gasket 77 in addition to the primary gasket 75.

Figure 14:
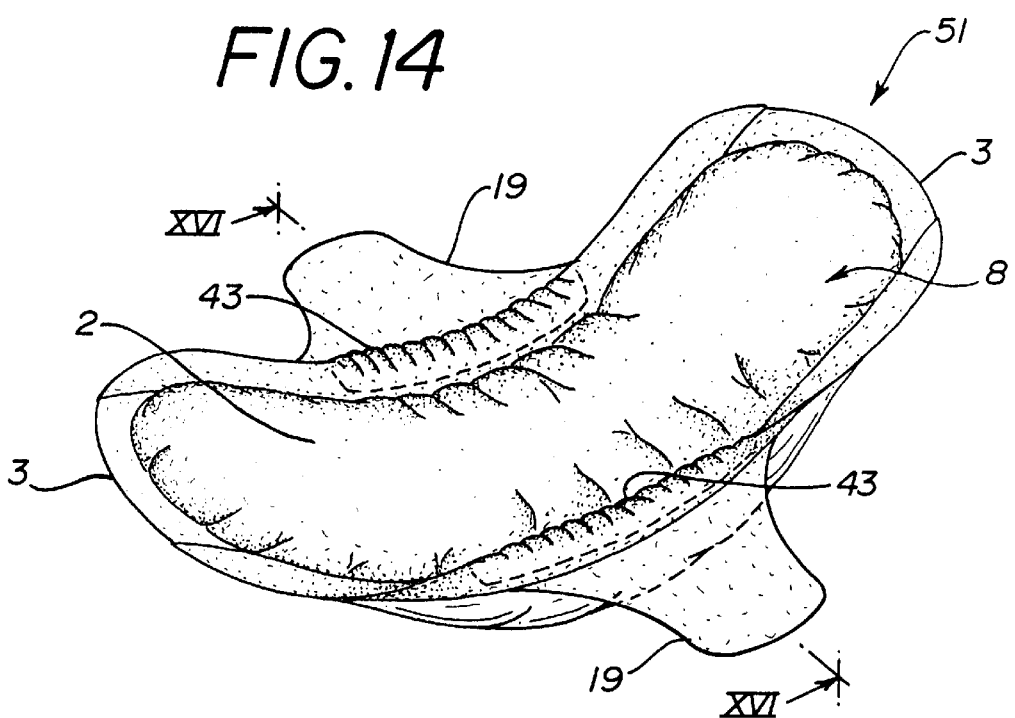
FIG. 14 is an isometric view of yet another embodiment of an absorbent article according to the current invention having wings.
Figure 15:
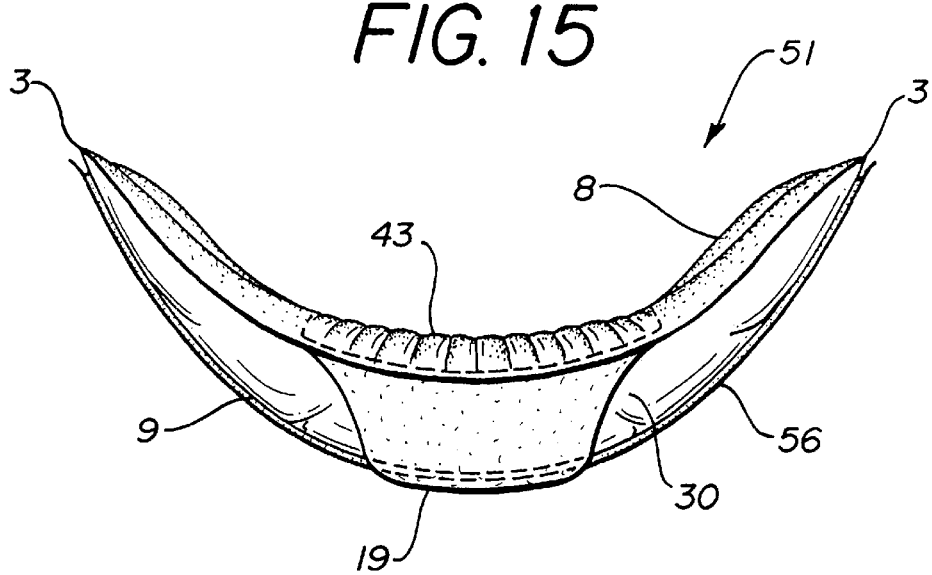
FIG. 15 is an elevation view of the article shown in FIG. 14.

As shown in FIGS. 14 and 15, the current invention may be advantageously adapted for use in a winged napkin 51. The wings 19 extend laterally outward from the napkin central portion 2. Although preferably not including absorbent pulp materials, the wings 19 may include a body fluid impervious backing such as the materials described in connection with the above-mentioned body fluid impervious barrier 9. It is also expected that the wings 19 can comprise a body fluid pervious material, much like the above-mentioned body fluid pervious cover 8. According to the current invention, the wings 19 are of the "cut and paste" type—that is, the wings are not integrally cut from the sheets of material forming the cover 8 and barrier 9 but are formed separately and attached to the central portion 2 via an adhesive. Such cut and paste wings are disclosed in U.S. Pat. No. 4,900,320 (McCoy), hereby incorporated by reference in its entirety. Consequently, the wing material need not be of the type suitable for a pervious cover 8 or an impervious barrier 9. A preferred method of forming the wings is disclosed in U.S. patent application Ser. No. 07/776,702, now abandoned, entitled "Absorbent Article With Attached Tabs and Method and Apparatus for Making Same", By Menard and Fung, hereby incorporated by reference in its entirety.

Figure 16:
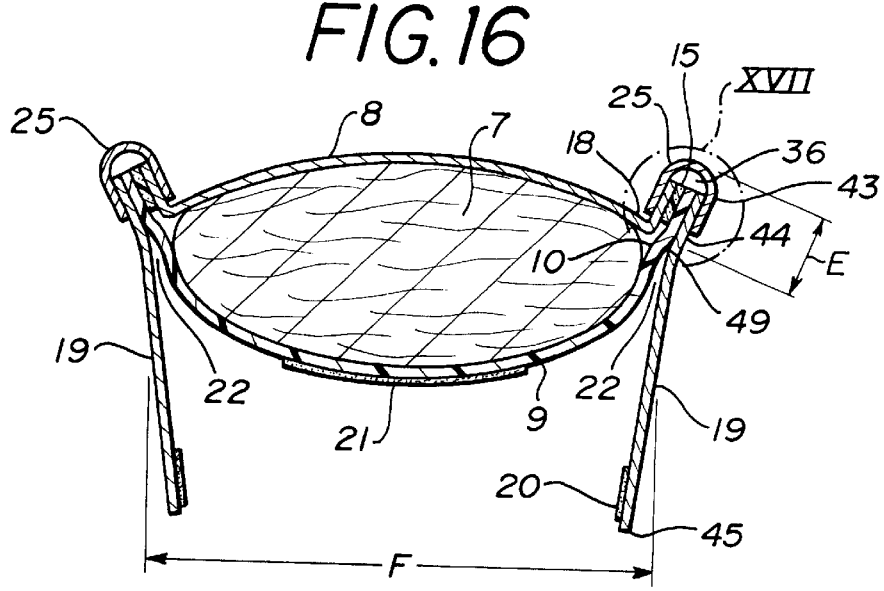
FIG. 16 is a transverse cross-section through the article shown in FIG. 14 taken through line XVI—XVI.

As shown in FIGS. 16 and 17, each gasket 43 is formed by joining the portions 10 and 18 of the barrier 9 and cover 10, respectively, adjacent their longitudinal edges together via an adhesive 34, thereby forming a flange. A compliant cuff 25 is formed by enclosing the flange or joined portion in a strip of material 55, such as that used to form the cuffs 48 shown in FIGS. 6 and 7. The cuff 25 may be attached so as to form a loop that encloses a cavity 36, as previously discussed, thereby giving it considerable compliancy. As before, the size and shape of the cavity 36 can be adjusted to control the compliancy of the gasket.

Figure 17A:
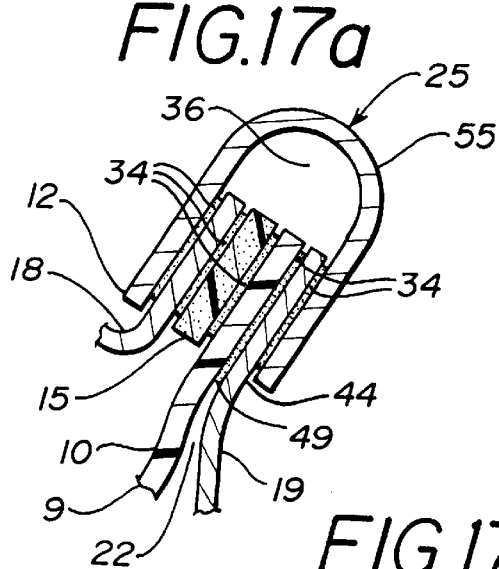
FIGS. 17 (a)–(c) are detailed views embodiments of the portion of the article shown in FIG. 16 enclosed by the circle XVII.
Figure 17B:
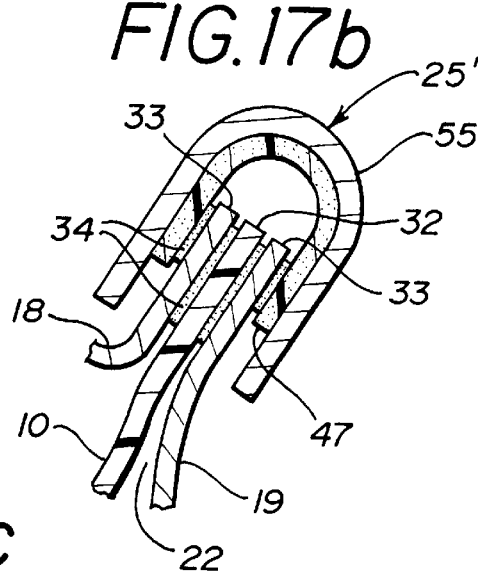
Figure 17C:
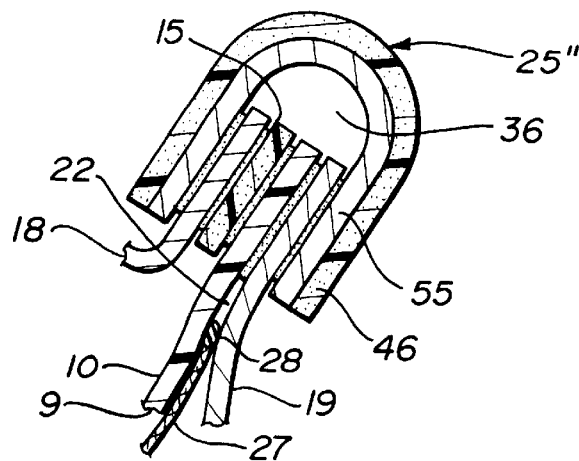

A strip of elastic foam 15, placed in tension when applied to the napkin, may be disposed between the barrier and cover portions 10 and 18, respectively, that form the flange so as to impart the aforementioned arcuate shape to the napkin, as shown in FIG. 17(a). Alternatively, as shown in FIG. 17(b), a strip of elastic foam 47 may be laminated to the interior surface of the strip of material 55 that forms the cuff 25', as previously discussed with respect to the embodiment shown in FIG. 6(a). As shown in FIG. 17(c), a cuff 25" could be formed by wrapping a layer of foam 46 around the strip of material 55 to impart further cushioning for the gasket. The layer of foam 46 could itself be elasticized and applied to the napkin in tension, thereby eliminating the need for the elastic foam 15 to impart the arcuate shape.

Importantly, wings 19 are attached to the central portion 2 so that they cooperate with the gaskets 43 in use, as explained further below. In the preferred embodiment, the base 44 of each wing 19 is attached to a flange, as shown in FIG. 17. Thus, as shown in FIG. 17(b), a first strip of adhesive 34 is disposed between the portion 18 of cover 8 adjacent its longitudinal edge 33 and the portion 10 of the barrier 9 adjacent its longitudinal edge 33 and a second strip of adhesive is disposed between the opposite surface of the portion 10 of the barrier and the base 44 of the wing 19 so that the flange and wing base form a unitary structure. Alternatively, heat sealing could be used in place of adhesive strips 34. As a result this arrangement, the cuff 25 encloses the wing base 44, giving a napkin having cut and paste wings a more aesthetically pleasing appearance. More importantly, this method of attaching the wings to the napkin provides certain functional benefits, as described below.

Figure 18:
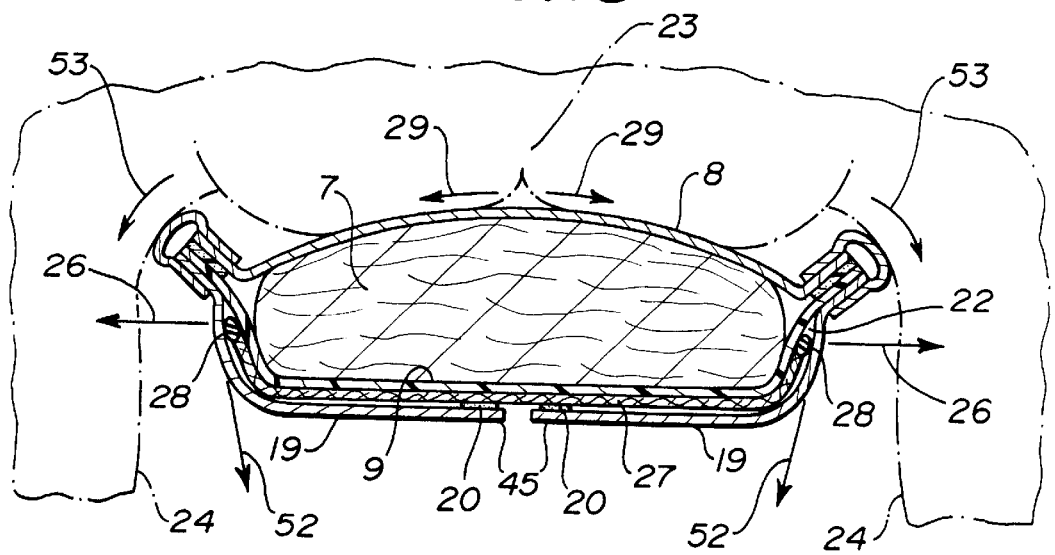
FIG. 18 is a transverse cross-section through the article shown in FIG. 14 in use.

In use, the wings 19 are folded downward around the crotch 27 so that the edges of the wing tips 45 nearly abut each other and are secured to the underside of the crotch 27 via the adhesive 20, as shown in FIG. 18. As is known in the art, the wings 19 serve to stabilize the napkin and protect the panty crotch 27 from side leakage. However, unlike the wings heretofore known in the art, when the user pulls the wings 19 according to the current invention around the edges of the panty crotch 27 and attaches them thereto by adhesive 20, downward forces 52 are applied to the gaskets through the wing bases 44. These downward forces 52 impose moments 53 that tend to rotate the gaskets downward, as shown in FIG. 18. This downward rotation prevents the gaskets from folding inward over the body facing surface 16 of the cover 8, thereby ensuring that effective placement of the gaskets is maintained. As previously discussed, the folding of the gaskets over the body facing surface 16 reduces its effective area. Thus, according to the current invention, the wings 19 serve to place both the central portion 2 and the gaskets 43 into good contact with the body.

Figure 19:
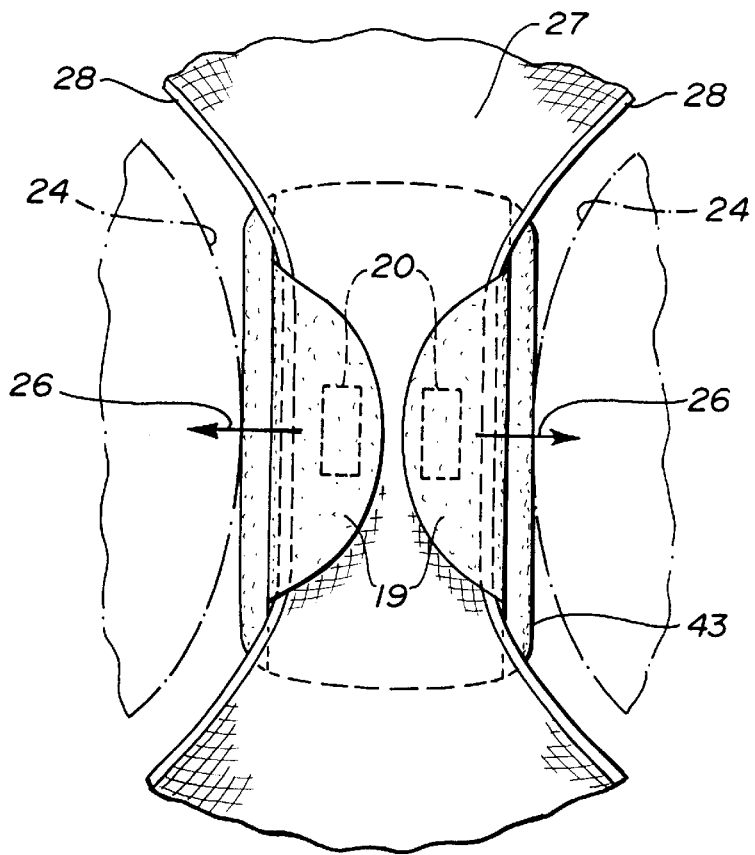
FIG. 19 is a plane view from below of the embodiment of the article shown in FIG. 14 in use.

In the embodiment shown in FIG. 16, the intersection 49 of the wing base 44 and the barrier 9 forms a pocket 22 disposed at, or slightly inward of, the proximal end of the gasket 43. As shown in FIGS. 17(c) and 18, the pockets 22 serve to retain the elasticized portions 28 on the edges of the panty crotch 27. According to the current invention, certain advantages are obtained by attaching the wings 19 so that the distance F, shown in FIG. 16, between the pockets 22 is less than the width of the panty crotch 27 when the crotch is in its undeformed state. Specifically, when the wings are attached to the panty crotch 27, as shown in FIGS. 18 and 19, the lateral compression of the crotch 27 causes the elastic 28 to impart outward acting forces 26 on the wings 19. Since the wing base 44, barrier portion 10 and cover portion 18 are joined together so as to act in unison, the forces 26 are transmitted from the wings 19 to the cover 8, thereby placing the cover in tension, indicated by arrows 29 in FIG. 18. This tension causes the cover 8 to be thrust upward so as to ensure good contact with the perineum 23. The tension also serves to prevent permanent deformation of the article due to lateral compression from the user's thighs since the panty elastic 28 acts as a spring to restore a laterally compressed central portion 2 to its undeformed shape.

Another advantage of the gasket/wing arrangement shown in FIGS. 16 and 17 is that the pockets 22, and therefore, the panty crotch elastic edges 28, are disposed below the base 12 of the gasket 43. As a result, the gaskets 43 extend a distance E, shown in FIG. 16, beyond the panty elastic. Unlike prior art attempts at sealing gaskets, the distance E is not limited to the thickness of the wing 19. Thus, the distal end 13 of the gasket makes sealing contact with the user's body regardless of the size of the user or the panty.

The napkin shown in FIG. 16 discloses another important aspect of the current invention. As is well known, the cover 8 can be formed from an apertured plastic film, such as Reticulon™, available from Chicopee Mills, Inc. of New York, N.Y., a division of Johnson & Johnson Corporation, or Dri-Weve™ by The Proctor & Gamble Company of Cincinnati, Ohio. Although such materials have the advantage of imparting a dry feeling, they are uncomfortable against the body, tending to produce a hot and sticky feeling, as previously discussed.

Figure 20:
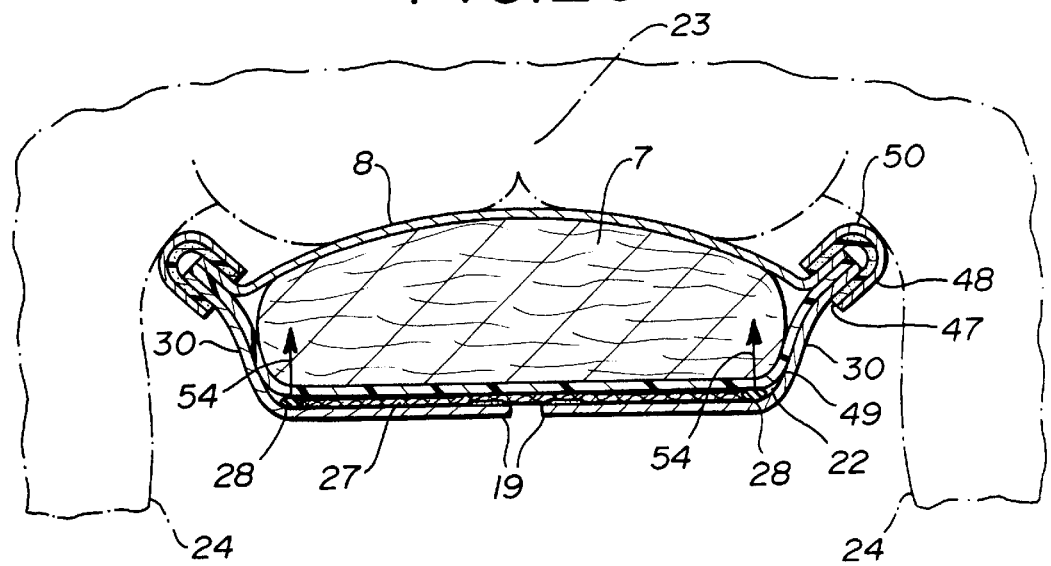
FIG. 20 is a transverse cross-section through another embodiment of the article shown in FIG. 14 in use.

Consequently, as shown in FIG. 16, according to the current invention, an apertured plastic film can be used only for the portion of the cover 8 directly over the absorbent core 7, where it is most beneficial. A second, more comfortable material can be used for the cuff 25 that bears against the body under pressure. Preferably this second material is a fibrous non-woven material, which, as is well known in the art, has a comfortable feeling against the body. Alternatively, a cuff 50 could be formed from a laminate of a layer 48 of a fibrous non-woven material and a layer of an elastic foam 47, as shown in FIG. 20. Use of such foam 47 can provide sufficient compliancy to the gasket so that the cavity 36 can be eliminated. Moreover, the elastic foam 47 can be placed in tension so as to impart an arcuate shape to the napkin, as previously discussed, thereby dispensing with the need for the elastic strips shown in FIG. 17.

According to the embodiment shown in FIG. 20, the wings 19 are attached to the barrier 9 so that, unlike the embodiment shown in FIG. 16, the initial intersection of the wings and the barrier occurs inboard of the longitudinally extending sides 30 of the central portion 2, thereby similarly disposing the pockets 22. In this configuration, the elastic portions 28 of the panty crotch 27 impart forces 54 which act directly against the central portion 2 to place it into good contact with the perineum 23.

Figure 21:
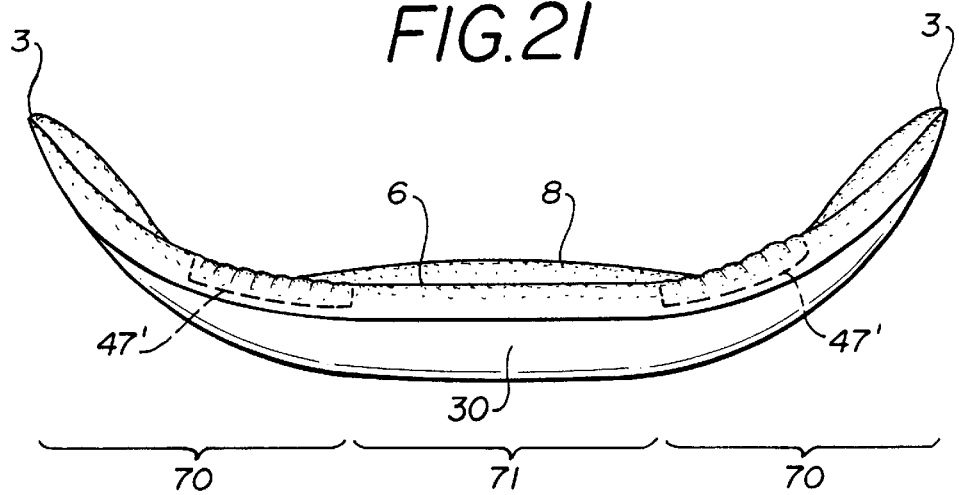
FIG. 21 is an elevation view of still another embodiment of the article shown in FIG. 1.

FIG. 21 shows another embodiment of the current invention in which segmented elastic members 47' are attached to the napkin in tension so as to impart a novel curvature to the napkin. The elastic segments 47' may be segments of elastic foam laminated within a gasket cuff, such as that discussed with respect to the embodiment shown in FIG. 6(a), or segments of elastic filaments 14 disposed within a gasket cuff cavity, such as that discussed with respect to the embodiment shown in FIG. 7(a), Alternatively, the elastic members may be heat shrinkable filaments applied to the napkin cover 8, as disclosed in aforementioned U.S. Pat. No. 3,236,238 (Morse), previously incorporated by reference.

According to the current invention, the novel curvature is obtained by applying the elastic segments 47' only to the end sections 70 that extend fore and aft from the longitudinally middle section 71 of the napkin. No elastic is applied to the middle section 71 itself. In the preferred embodiment, the middle section 71 comprises at least 25% of the napkin length. Thus, unlike the continuously curved arcuate shape heretofore known in the art, the napkin according to the current invention consists of a substantially straight middle section 71 having arcuate sections 70 extending therefrom both fore and aft, as shown in FIG. 21.

The napkin shape shown in FIG. 21 has several important advantages. First, the wrinkling associated with shaping is confined to the end sections 70 so that the middle section 71, which is in direct contact with the perineum and directly exposed to fluid flow, is free of wrinkles. The absence of wrinkling provides a more comfortable body facing surface against the skin and avoids the formation of transverse channels that encourage the fluid to flow laterally out of the central portion 2 of the napkin. In addition, wrinkling can result in several portions of the cover folding over itself so that the fluid tends to wick to the napkin sides rather than penetrate into the central absorbent 7. Second, forces imposed by the user's body on the ends 3 of the napkin tend to thrust the middle section 71 upward into good contact with the perineum. Third, the absence of elastic in the gaskets in the middle section 71 allows the gaskets to splay outward so that they are less likely to fold over the body facing surface in use.

As the foregoing indicates, the method of the current invention affords great flexibility in the design of sanitary napkins, allowing the use of a wide range of gasket materials and allowing the gaskets to be attached to the napkin in various ways to achieve an optimum configuration. Moreover, although the invention has been explained with reference to a sanitary napkin, the invention is also suitable for use in other absorbent articles, such as incontinence pads and the like. As the various embodiments disclosed above indicate, the present invention may be embodied in many specific forms without departing from the spirit or essential attributes thereof and, accordingly, reference should be made to the appended claims, rather than to the foregoing specification, as indicating the scope of the invention.

LIST OF REFERENCE NUMERALS

1 Sanitary napkin
2 Central portion
3 Transverse ends
6 Gaskets
7 Absorbent core
8 Cover
9 Barrier
10 Portion of barrier adjacent edge
11 Strip
12 Base of gasket
13 Distal end of gasket
14 Elastic elements
15 Elastic foam
16 Body facing surface
17 Garment facing surface
18 Portion of cover adjacent edge
19 Wing
20 Wing adhesive
21 Central portion adhesive
22 Pocket
23 Perineum
24 Side of thigh
25 Cuff
26 Force from elastic
27 Panty crotch
28 Elasticized portion of panty crotch
29 Opposing forces in cover
30 Longitudinal sides
32 Edge of barrier
33 Edge of cover
34, 35 Adhesive
36 Cavity
37 Force from thighs
38, 39 Laminate layers 40–43 Gaskets
44 Base of wing
45 Tip of wing
46 Foam
47 Elastic foam
48 Layer of cuff
49 Juncture of wing and barrier
50 Flange
51 Winged napkin
52 Force
53 Moment
54 Force
55 Strip of material
56 Release strip

What is claimed is:

1. An absorbent article adapted to be worn in a crotch portion of a user's undergarment for use in the perineal area of the user's body to absorb fluid, comprising:
   a) a longitudinally extending central portion having (i) an absorbent core, (ii) a first layer covering at least a portion of said absorbent core and forming a body facing surface, said first layer having right and left approximately longitudinally extending edges, and (iii) a second layer covering at least a portion of said absorbent core and forming a second surface opposite said body facing surface, said second layer having right and left approximately longitudinally extending edges; and
   b) right and left hand approximately longitudinally extending gaskets for preventing lateral leakage of said fluid, each of said gaskets comprising (i) a longitudinally extending portion of said first layer adjacent one of its said edges, (ii) a longitudinally extending portion of said second layer adjacent one of its said edges joined to said portion of said first layer so as to form a flange, and (iii) a strip of material enclosing at least a portion of said flange; wherein said strip of material comprises a layer of flexible fabric and a layer of elastic foam laminated to said layer of flexible fabric and wherein said gaskets are pre-formed to extend outward from said central portion.

2. The absorbent article according to claim 1, wherein said first layer is formed from an apertured plastic film and said strips of material comprise a layer of fibrous non-woven material.

3. The absorbent article according to claim 1, wherein each of said strips of material forms a cavity between said strips of material and said longitudinally extending edges of said first and second layers.

4. The absorbent article according to claim 3, wherein each of said cavities forms a compliant portion of its respective gasket that is configured to deform in response to compressive forces imparted by said user's body.

* * * * *